(12) United States Patent
Marcus et al.

(10) Patent No.: US 10,281,405 B2
(45) Date of Patent: May 7, 2019

(54) AMBIENT DESORPTION-OPTICAL EMISSION SPECTROSCOPY USING A MICROPLASMA DESORPTION/EXCITATION SOURCE

(71) Applicant: CLEMSON UNIVERSITY, Clemson, SC (US)

(72) Inventors: Richard Kenneth Marcus, Clemson, SC (US); Htoo Wai Paing, Charleston, SC (US); Xinyan Zhang, Central, SC (US)

(73) Assignee: Clemson University Research Foundation, Clemson, SC (US)

( * ) Notice: Subject to any disclaimer, the term of this patent is extended or adjusted under 35 U.S.C. 154(b) by 0 days.

(21) Appl. No.: 15/399,916

(22) Filed: Jan. 6, 2017

(65) Prior Publication Data

US 2017/0199130 A1   Jul. 13, 2017

Related U.S. Application Data

(60) Provisional application No. 62/276,364, filed on Jan. 8, 2016.

(51) Int. Cl.
*G01N 21/67* (2006.01)
*G01N 21/69* (2006.01)

(52) U.S. Cl.
CPC ............. *G01N 21/69* (2013.01); *G01N 21/67* (2013.01); *G01N 2201/0221* (2013.01)

(58) Field of Classification Search
CPC ................... G01N 21/69; G01N 21/67; G01N 2201/0221; H01J 37/32972; H01J 49/142
See application file for complete search history.

(56) References Cited

U.S. PATENT DOCUMENTS

| 5,086,226 | A | 2/1992 | Marcus |
| 5,325,021 | A | 6/1994 | Duckworth et al. |
| 6,750,449 | B2 | 6/2004 | Marcus |
| 6,852,969 | B2 | 2/2005 | Marcus et al. |
| 9,536,725 | B2 | 1/2017 | Marcus et al. |
| 2004/0022677 | A1* | 2/2004 | Wohlstadter .......... B01L 3/5085 422/52 |
| 2014/0218729 | A1* | 8/2014 | Marcus .................. H01J 49/105 356/316 |

OTHER PUBLICATIONS

Marcus, R.K., Burdette, C.Q., Manard, B.T. et al. Anal Bioanal Chem (2013) 405: 8171, "Ambient desorption/ionization mass spectrometry using a liquid sampling—atmospheric glow discharge (LS-APGD) ionization source".*

(Continued)

*Primary Examiner* — Dominic J Bologna
(74) *Attorney, Agent, or Firm* — Dority & Manning, P.A.

(57) ABSTRACT

Described is an elemental analysis system and methods for use thereof that can be utilized in examination of samples in their native state. The systems utilize a liquid sampling—atmospheric pressure glow discharge (LS-APGD) device for ambient desorption sampling and excitation of a solid sample in combination with optical emission detection. This approach can find application across a broad spectrum of analytical challenges including metals, soils, and volume-limited samples.

20 Claims, 6 Drawing Sheets

(56) References Cited

OTHER PUBLICATIONS

Takats Z, Wiseman JM, Gologan B, Cooks RG. Mass spectrometry sampling under ambient conditions with desorption electrospray ionization. Science. Oct. 15, 2004;306(5695):471-473.
Cody RB, Laramée JA, Durst HD. Versatile new ion source for the analysis of materials in open air under ambient conditions. Analytical chemistry. Apr. 15, 2005;77(8):2297-302.
Venter A, Nefliu M, Cooks RG. Ambient desorption ionization mass spectrometry. TrAC Trends in Analytical Chemistry. Apr. 30, 2008;27(4):284-290.
Harris GA, Galhena AS, Fernandez FM. Ambient sampling/ionization mass spectrometry: applications and current trends. Analytical Chemistry. May 6, 2011;83(12):4508-4538.
Shelley JT, Wiley JS, Hieftje GM. Ultrasensitive ambient mass spectrometric analysis with a pin-to-capillary flowing atmospheric-pressure afterglow source. Analytical chemistry. Jul. 15, 2011;83(14):5741.
Albert A, Shelley JT, Engelhard C. Plasma-based ambient desorption/ionization mass spectrometry: state-of-the-art in qualitative and quantitative analysis. Analytical and bioanalytical chemistry. Oct. 1, 2014;406(25):6111-6127.
Shelley JT, Hieftje GM. Ambient mass spectrometry: Approaching the chemical analysis of things as they are. Journal of Analytical Atomic Spectrometry. 2011;26(11):2153-2159.
Takats Z, Wiseman JM, Cooks RG. Ambient mass spectrometry using desorption electrospray ionization (DESI): instrumentation, mechanisms and applications in forensics, chemistry, and biology. Journal of Mass Spectrometry. Oct. 1, 2005;40(10):1261-1275.
Jones RW, Cody RB, McClelland JF. Differentiating writing inks using direct analysis in real time mass spectrometry. Journal of forensic sciences. Jul. 1, 2006;51(4):915-918.
Sampson JS, Muddiman DC. Atmospheric pressure infrared (10.6 μm) laser desorption electrospray ionization (IR-LDESI) coupled to a LTQ Fourier transform ion cyclotron resonance mass spectrometer. Rapid Communications in Mass Spectrometry. Jul. 15, 2009;23(13):1989-1992.
Li H, Smith BK, Márk L, Nemes P, Nazarian J, Vertes A. Ambient molecular imaging by laser ablation electrospray ionization mass spectrometry with ion mobility separation. International Journal of Mass Spectrometry. Feb. 1, 2015;377:681-689.
Shelley JT, Ray SJ, Hieftje GM. Laser ablation coupled to a flowing atmospheric pressure afterglow for ambient mass spectral imaging. Analytical chemistry. Oct. 1, 2008;80(21):8308-8313.
Davis WC, Marcus RK. An atmospheric pressure glow discharge optical emission source for the direct sampling of liquid mediaPresented at the 2001 European Winter Conference on Plasma Spectrochemistry, Lillehammer, Norway, Feb. 4-8, 2001. Journal of Analytical Atomic Spectrometry. 2001;16(9):931-937.
Venzie JL, Marcus RK. Effects of easily ionizable elements on the liquid sampling—atmospheric pressure glow discharge. Spectrochimica Acta Part B: Atomic Spectroscopy. Jun. 30, 2006;61(6):715-721.
Manard BT, Gonzalez JJ, Sarkar A, Dong M, Chirinos J, Mao X, Russo RE, Marcus RK. Liquid sampling-atmospheric pressure glow discharge as a secondary excitation source: assessment of plasma characteristics. Spectrochimica Acta Part B: Atomic Spectroscopy. May 1, 2014;94:39-47.
Manard BT, Konegger-Kappel S, Gonzalez JJ, Chirinos J, Dong M, Mao X, Marcus RK, Russo RE. Liquid Sampling—Atmospheric Pressure Glow Discharge as a Secondary Excitation Source for Laser Ablation-Generated Aerosols: Parametric Dependence and Robustness to Particle Loading. Applied spectroscopy. Jan. 2015;69(1):58-66.
Marcus RK, Quarles Jr CD, Barinaga CJ, Carado AJ, Koppenaal DW. Liquid sampling-atmospheric pressure glow discharge ionization source for elemental mass spectrometry. Analytical chemistry. Feb. 28, 2011;83(7):2425-2429.
Zhang LX, Manard BT, Kappel SK, Marcus RK. Evaluation of the operating parameters of the liquid sampling-atmospheric pressure glow discharge (LS-APGD) ionization source for elemental mass spectrometry. Analytical and bioanalytical chemistry. Nov. 1, 2014;406(29):7497-509.
Konegger-Kappel S, Manard BT, Zhang LX, Konegger T, Marcus RK. Liquid sampling-atmospheric pressure glow discharge excitation of atomic and ionic species. Journal of Analytical Atomic Spectrometry. 2015;30(1):285-295.
Marcus RK, Burdette CQ, Manard BT, Zhang LX. Ambient desorption/ionization mass spectrometry using a liquid sampling—atmospheric glow discharge (LS-APGD) ionization source. Analytical and bioanalytical chemistry. Oct. 1, 2013;405(25):8171-8184.
Zhang LX, Manard BT, Powell BA, Marcus RK. Preliminary Assessment of Potential for Metal—Ligand Speciation in Aqueous Solution via the Liquid Sampling—Atmospheric Pressure Glow Discharge (LS-APGD) Ionization Source: Uranyl Acetate. Analytical chemistry. Jul. 2, 2015;87(14):7218-7225.
Harris GA, Hostetler DM, Hampton CY, Fernández FM. Comparison of the internal energy deposition of direct analysis in real time and electrospray ionization time-of-flight mass spectrometry. Journal of the American Society for Mass Spectrometry. May 31, 2010;21(5):855-863.
Salter TL, Gilmore IS, Bowfield A, Olabanji OT, Bradley JW. Ambient surface mass spectrometry using plasma-assisted desorption ionization. effects and optimization of analytical parameters for signal intensities of molecules and polymers. Analytical chemistry. Jan. 18, 2013;85(3):1675-1682.
Weston DJ. Ambient ionization mass spectrometry: current understanding of mechanistic theory; analytical performance and application areas. Analyst. 2010;135(4):661-668.
Marcus RK, Davis WC. An atmospheric pressure glow discharge optical emission source for the direct sampling of liquid media. Analytical chemistry. Jul. 1, 2001;73(13):2903-2910.

\* cited by examiner

AMBIENT DESORPTION-OPTICAL EMISSION SPECTROSCOPY USING A MICROPLASMA DESORPTION/EXCITATION SOURCE

CROSS REFERENCE TO RELATED APPLICATION

This application claims filing benefit of U.S. Provisional Patent Application Ser. No. 62/276,364 having a filing date of Jan. 8, 2016, which is incorporated herein by reference in its entirety.

STATEMENT REGARDING FEDERALLY SPONSORED RESEARCH OR DEVELOPMENT

This invention was made with government support under Grant No. HDTRA1-14-1-0010 awarded by the DoD/DTRA. The government has certain rights in the invention.

BACKGROUND

One of the most active fields within analytical chemistry is ambient desorption/ionization-mass spectrometry (ADI-MS) due to the capacity to "analyze things as they really are". A plethora of ADI source designs have been described in the literature, with most seeking to affect the sampling (volatilization) of a solid under ambient conditions with subsequent ionization in the gas phase by the same or a supplemental form of energy. The most evolved of these approaches include desorption electrospray ionization (DESI) and direct analysis in real time (DART) sources. These approaches typically include low temperature (<100° C.) volatilization of molecular species from a surface such that there is minimal thermal degradation and soft ionization via proton addition, with each component affected by different processes. The sampling is fairly diffuse, not having a high level of lateral resolution/selectivity in comparison to microprobe methods. Regiospecific sampling can be affected through the use of other steps, such as a laser vaporization step.

The use of the liquid sampling-atmospheric pressure glow discharge device (LS-APGD) as an ionization source for analysis via mass spectrometry has been demonstrated in both an ADI-MS mode and as a molecular ionization source. The LS-APGD has been recognized as a low power, low sample consumption microplasma source alternative to the inductively coupled plasma (ICP), and has been a successful source for miniaturized instrumentation platforms.

Independent of the energy source(s) for the sampling and ionization components of the ADI-MS process, once the sample is volatized and ionized, it is characterized by mass spectrometry, which requires the ionic species of the sample to be extracted and directed to the analyzer. Unfortunately, use of mass spectrometry requires that the analytical process be a multi-step process in which the sample is initially volatized and ionized (which can be a two-step process in itself) and then relocated for final analysis in the MS step. The multi-step process increases analytic complexity and introduces potential for error to the protocol.

Moreover, the complexity and instrumentation sensitivity of mass spectrometry, as well as that of many of the possible ADI protocols, are not conducive to many analytical applications such as sample analysis in the field. Applications to date tend to be in the qualitative analysis of species adsorbed to surfaces, such as pesticides on foodstuffs, drug residues on currency, and small molecule components of bulk materials such as pharmaceuticals, with protocols requiring sample transport and preparation in the lab, which introduces the possibility of contamination and further complicates the analysis protocols.

What are needed in the art are analytical systems and methods that can provide accurate and consistent results with small sample sizes and that can operate at low cost and low energy consumption. A single-step analytic approach that can be portable for use in the field would also be of great benefit.

SUMMARY

According to one embodiment, disclosed is a method for examining a sample. More specifically, a method can include forming a microplasma in a glow discharge space by use of an LS-APGD device. Upon formation, the microplasma can contact a solid sample that is within the glow discharge space so as to volatize the solid sample and release components, e.g., molecules, from the sample and excite the released components in a single step. The excited sample can then emit a characteristic response while still in the glow discharge space. The method also includes detecting this characteristic response via optical emission spectroscopy as the emission occurs within the glow discharge space.

Also disclosed is a system for examining a solid sample. For instance, the system can include an LS-APGD device. The LS-APGD device includes a hollow capillary (or tube) that is configured to carry an electrolyte solution from an electrolyte solution source to a discharge end of the hollow capillary. The LS-APGD device also includes a counter electrode disposed at a distance from the discharge end of the hollow capillary and a power source in electrical communication with the counter electrode. The distance between the discharge end of the hollow capillary and the counter electrode defines the glow discharge space of the LS-APGD device. The LS-APGD device also includes a stage within the glow discharge space that is configured to carry a solid sample during an analysis protocol. In addition, the system includes a detector such as an optical emission spectrometer in optical communication with the glow discharge space.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to the development of a facile, economical, and, in some embodiments, portable, elemental analysis system and methods for use thereof that can be utilized in examination of samples in their native state. More specifically, disclosed systems utilize LS-APGD devices for ambient desorption sampling and excitation in combination with optical emission detection to provide a single-step process that does not require the relocation of the sample material to the analyzing device during the protocol. This approach can find application across a broad spectrum of analytical challenges requiring elemental analysis, including metals, soils, and volume-limited samples, analogous to what has been seen in the development of the field of ADI-MS for molecular species determinations.

During use, the microplasma formed by use of the LS-APGD device affects both the volatilization and excitation of sample components. The precise mechanism of vaporization remains to be determined, but no matter the mechanism, reduction of analyte species down to atomic form, followed by electronic excitation, is affected by the plasma itself as demonstrated in the examples herein. The system can be utilized with any sample matrix forms including, without limitation, vapor-deposited metallic thin films, dried solution residues, and bulk metals.

The ability to affect direct sampling with no sample preparation required and optical emission spectroscopy (OES) analysis of diverse surfaces in a single step with a relatively simple system provides a route to wide-ranging applications such as non-proliferation, geochemistry, and metal sourcing. Beneficially, the systems can provide simplicity in terms of both operational overhead and general utility.

Figure 1:
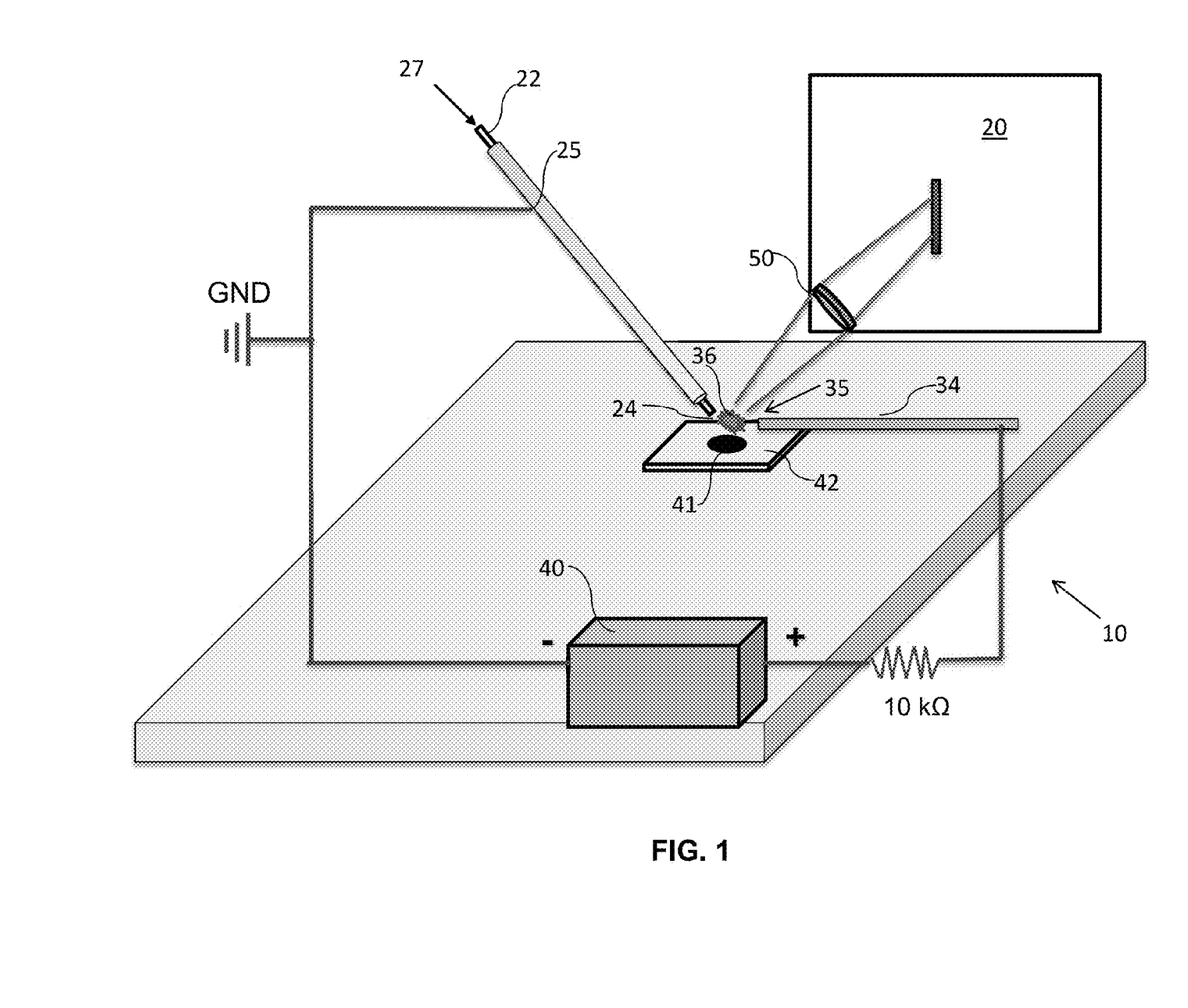
FIG. 1 is a diagrammatic representation of a system as disclosed herein.

One embodiment of a system is illustrated in FIG. 1. As shown, a system can include an LS-APGD device 10 in conjunction with an OES device 20. The LS-APGD is a low power, small footprint source that has been used in analytical techniques in the past (see, e.g., U.S. Pat. Nos. 6,852,969, 6,750,449, 5,325,021, 5,086,226, and 5,006,706, and U.S. Patent Application Publication No. 2014/0218729, all of which are incorporated herein by reference). The microplasma of an LS-APGD generally operates at power densities of about 10 W/mm$^3$. LS-APGD was originally developed for applications in metal speciation, being operable at low solution flow rates (<400 µL/min) and employing an electrolytic solution (e.g., 5% acid/salt) as the mobile phase. In the previously known direct solution analysis mode, heat is generated as current flows across the air/liquid interface and causes evaporation, eventually culminating in excitation of the analyte species that is carried in a fluid flow passing through the microplasma. For quantitative analysis, detection limits for aqueous samples are at the single nanogram level using relatively simple optical spectrometer systems. The microplasma environment (e.g., kinetic and excitation temperatures) is more in line with combustion flames than other atmospheric pressure plasmas (e.g. ICPs). The robustness of the microplasma with regard to changes in solution matrices is similar to ICP sources. The use of LS-APGD has positive attributes in terms of design simplicity, small footprint, low operating powers, and very low liquid flow rates resulting in no liquid waste. Building on the development of the low power microplasma, the LS-APGD source has brought compactness and low gas and sample consumption to the elemental analysis of flowing samples and brings such attributes to the disclosed elemental analysis of solid samples.

In the disclosed systems, and in contrast to previously known LS-APGD liquid sampling systems and methods, an LS-APGD device can volatize and excite a sample from the solid phase. For instance, and as illustrated in FIG. 1, disclosed systems are configured such that a sample 41 can be provided in the solid phase and can be held, e.g., on a stage 42, such that a microplasma 36 formed in a glow discharge space 35 can contact the sample 41. Upon contact, an amount of the sample 41 can be volatized to release components, e.g., atoms or molecules, of the solid sample and the released components can be excited. Solid samples of various size and shape can be probed, though the area sampled is set by the size of the plasma volume 36. For example, in some embodiments, residues of solutions of about 1 µL dried on a solid support can be sampled.

The stage 42 (or when no stage is necessary, the solid sample 41 itself) can in one embodiment be mobile, for instance by use of a stepper motor, which can cause the sample 41 to move as desired in one, two, or three directions, for instance in steps of about 1 millimeter or less. This can be beneficial in providing desired contact between the microplasma 36 and the solid sample 41 to encourage volatilization and excitation.

In one embodiment, the surface of the sample 41 can be electrically isolated (floating) relative to the discharge electrodes 37, 34 of the LS-APGD device 10, and as such there will be no directed charged particle interactions that might result in sputtering, etc.

There is no particular limit to the solid samples that can be examined by use of disclosed systems. For instance, while in many embodiments, the sample 41 can be electrically conductive, e.g., when examining a metal sample, there is no requirement that the sample 41 be electrically conductive. Moreover, in some embodiments, the sample 41 can be a component of the circuit that forms the microplasma 36.

As shown in FIG. 1, the LS-APGD device can include a power supply 40. The LS-APGD device also includes a capillary 22 generally in the form of a hollow cylindrical tube, through which an electrolyte solution 27 can flow. The electrolyte solution 27 can include any acid or salt capable of accepting electric charge and developing the desired voltage difference in conjunction with the counter electrode. By way of example, the electrolyte solution can be an aqueous solution of an acid, e.g., a nitric acid solution.

In one embodiment, the electrolyte solution can contain a reference material, for instance a known amount of the analyte or another material that can function as an internal standard during use of the device/system. The reference material can be excited within the glow discharge space in conjunction with the volatilized sample and this emission can also be detected by the optical detection device. This detection can provide a standard for comparison with the analyte and can thereby provide information with regard to the particular analyte species, concentration, etc. that has been volatilized from the solid sample.

The discharge end 24 of the capillary 22 is a free end that can terminate in a plane that is generally perpendicular to the axis of fluid flow upon exiting of the discharge end 24 of the capillary 22. The inside diameter of the capillary 22 can be of a size to deliver the relatively low volumes of electrolyte solution 27 utilized in the disclosed methods. For instance, the inside diameter of the capillary 22 can be from about 0.1 mm to about 2 mm, or from about 0.2 mm to about 0.5 mm in some embodiments.

The LS-APGD generally can also include a mechanism (not shown in FIG. 1) for moving the electrolytic solution 27 so as to be expelled from the discharge end 24 of the capillary 22. For instance, the electrolytic solution 27 can be expelled from the discharge end 24 of the capillary 22 at a rate in the range of about 1 microliter per minute (µL/min) to about 5 milliliter per minute (mL/min) at atmospheric pressure. Flow through the hollow capillary 22 can be accomplished in a number of ways. For example, a high precision liquid pumping system such as a high performance liquid chromatography (HPLC) pump can be utilized for moving the electrolyte solution 27 through the hollow capillary 22. The inlet end of the capillary 22 can be connected in fluid communication with the outlet of a pump. One example of such a suitable HPLC pump is a Waters (Milford, Mass.) Model 510 HPLC pump.

In another embodiment, flow through the capillary can be encouraged by inducing electro-osmotic flow. In this embodiment, a direct current power supply can place an electric potential along the length of a section of the capillary 22 that terminates in the discharge end 24. An electric field thus established causes positively charged particles inside the capillary 22 to migrate toward the discharge end 24. As the positively charged particles move, they carry along any non-charged species due to the effect of the fluid's viscosity, and momentum carries the fluid 27 out of the discharge end 24 of the capillary 22. In yet another embodiment, flow through the capillary can be accomplished by capillary action, i.e., wicking.

The LS-APGD device 10 also includes a counter electrode 34. A terminus of the counter electrode 34 is disposed at a predetermined distance from the discharge end 24 of the hollow capillary 22 forming a glow discharge space 35 in which the microplasma 36 is formed. For example, the distance between the terminus of the counter electrode 34 and the discharge end 24 of the capillary 22 that defines the glow discharge space 35 can be from about 0.1 mm to about 5 mm, e.g., about 2 mm. The size of the glow discharge space can also be variable on a device. For instance, the discharge end 24 of the hollow capillary 22 can be selectively movable with regard to the counter electrode 34 so that the size and/or configuration of the glow discharge space 35 can be varied.

The capillary 22 and the counter electrode 34 can be aligned in any desired configuration. For instance, a particular configuration between the two can be provided to more effectively provide contact between the microplasma 36 formed in the glow discharge space 35 and the solid sample 41 and/or to detect the optical emissions from the volatilized, excited sample. By way of example, the discharge end 24 of the capillary 22 can be disposed such that the longitudinal axis of the capillary 22 at the discharge end 24 is in axial alignment with an axis of the counter electrode 34, and this axial alignment can be in any plane. In one embodiment, an axial alignment of the capillary 22 and the counter electrode 34 can serve to improve containment of the microplasma 36 formed in the glow discharge space 35 and may increase retention time of an analyte within the microplasma 36. However, this is not a requirement and in other embodiments, a longitudinal axis of the counter electrode 34 can be disposed at an angle to the axial direction of electrolyte flow 27 from the discharge end 24 of the capillary 22. This angle can be varied depending upon the system parameters. For instance the angle between the longitudinal axis of the hollow capillary 22 and a longitudinal axis of the counter electrode 34 can be less than 90°, about 90°, or greater than 90°.

Figure 2:
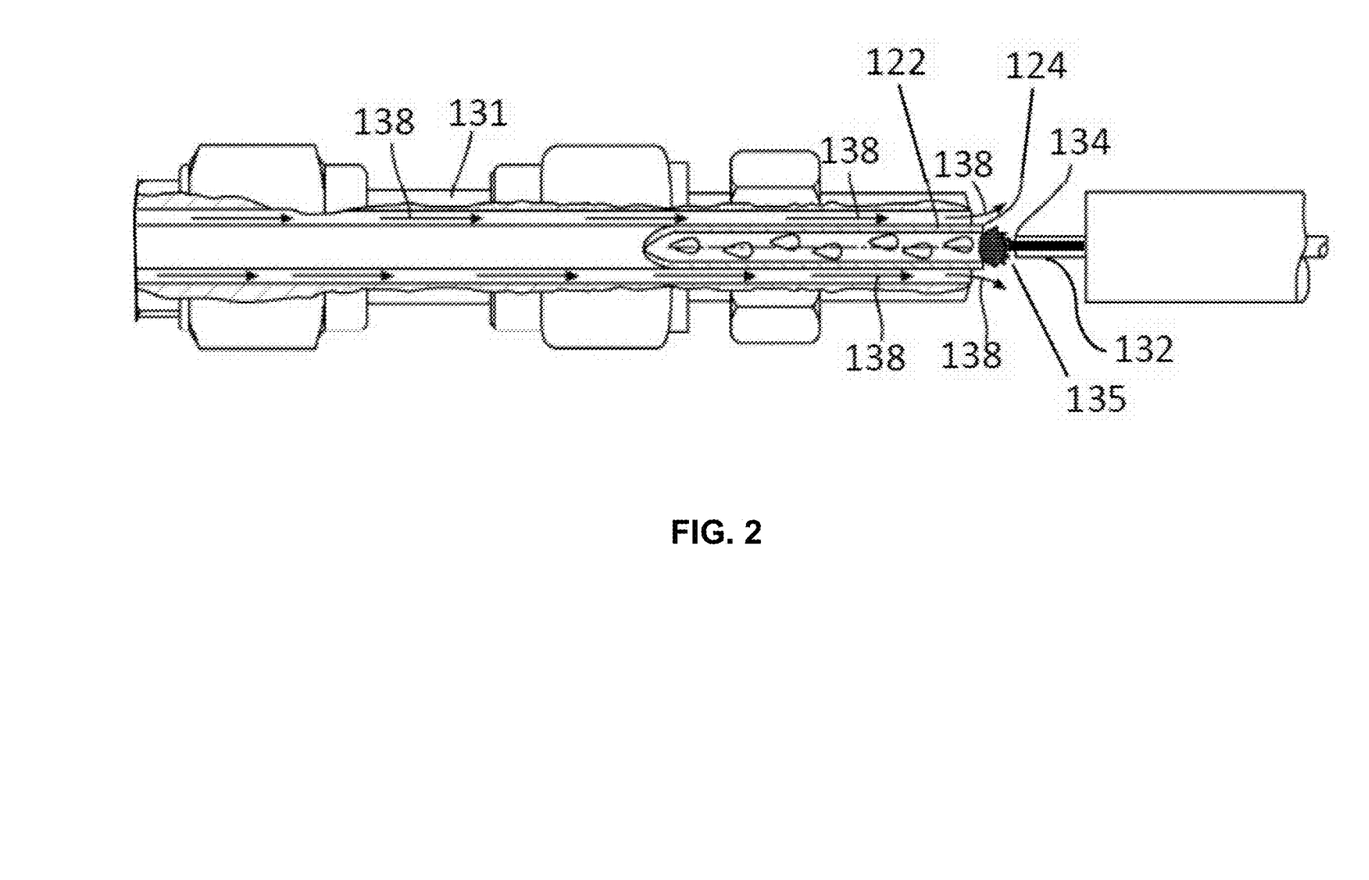
FIG. 2 is a diagrammatic representation of a portion of another embodiment of a system as disclosed herein.

While the counter electrode 34 can be a solid component as illustrated in FIG. 1, in some embodiments such as that illustrated in FIG. 2, the counter electrode 134 can be a terminal portion of a second hollow capillary 132. In this embodiment, an inert flow such as argon, nitrogen, or helium through the second hollow capillary 132 during use can provide a more robust and stable microplasma in the glow discharge space 135. As with a system that utilizes a solid counter electrode, the glow discharge space 135 can be defined within the distance between the discharge end 124 of the first hollow capillary 122 and the discharge end 134 of the second hollow capillary 132. In the embodiment of FIG. 2, which includes the second hollow capillary 132, the glow discharge space 135 can encompass that area in which the electrolyte flow that is discharged from the first hollow capillary 122 and the inert flow that is discharged from the second hollow capillary 132 will intersect.

In those embodiments in which the counter electrode is an end portion of a second hollow capillary, at least the discharge end 134 of the second hollow capillary 132 can include a conductive material, for instance a metal such as stainless steel, copper, etc. to form the counter electrode of the device. Additionally, a second capillary 132, when present, can be of a size that is in the same range as the primary capillary 122, e.g., from about 0.1 mm to about 2 mm, or from about 0.2 mm to about 0.5 mm in some embodiments. However, the two capillaries need not be of the same size, materials, or shape as one another.

When present, flow through a second capillary 134 can generally be in the range of from about 0.1 L/min to about 1 L/min, for instance from about 0.15 L/min to about 0.8 L/min, from about 0.2 L/min to about 0.7 L/min, or from about 0.3 L/min to about 0.6 L/min, in some embodiments.

Referring again to FIG. 1, the power supply 40 is in electrical conduct with a conductive element 25 (for instance an electrically conductive capillary section) in the hollow capillary 22 that during use is in electrical communication with the electrolyte solution 27 within the capillary 22. Thus, the electrolyte solution 27 and the counter electrode 34 form the input and output electrodes of the LS-APGD apparatus.

The power supply 40 is not particularly limited. For instance, the power supply can be a direct current source. In other embodiments, the power supply can be a radio frequency power source, a microwave frequency power source, or any other suitable power source as is generally known in the art. A suitable direct current power source for maintaining the glow discharge can be provided by a Kepco (Flushing, N.Y.) Model BHA 2000-0.1M power supply. In one embodiment, the same power supply that is used to move the electrolyte solution 27 through the capillary 22 (e.g., via electro-osmosis) can be used to provide the power needed to maintain the microplasma 36 that is produced at the glow discharge space 35.

The specific design of the electrical system is not particularly limited as long as the electrolyte solution 27 that will be carried within the capillary 22 can function as an electrode during use. For instance, in one embodiment, the discharge end 24 of the hollow capillary 22 can be formed of a material that is electrically conductive, such as a metal, e.g., stainless steel, and the power supply 40 can be connected at the discharge end. This is not a requirement of the device, however, and the discharge end 24 of the capillary 22 can alternatively be formed of a material that is electrically insulating (such as a polymer (e.g., PEEK) glass or fused silica for example) and/or material that is electrically semi-conducting (such as silicon). In this embodiment, the hollow capillary 22 can include an electrically conductive element 25 (such as a capillary section, for instance) at a point upstream of the discharge end 24 as illustrated in FIG. 1.

The electrical connections between the power supply 40, an electrically conductive element 25 of the first hollow capillary 22, and the counter electrode 34 can be utilized to establish a potential difference across the electrolyte solution 27 that functions as a solution electrode and the counter electrode 34 to form the microplasma 36. For example, the system can be configured so as to place a potential difference in the range of from about 200 volts to about 1,000 volts (direct current) across the electrolyte solution as it exits the discharge end 24 of the hollow capillary 22 and the counter electrode 34.

The polarity of the system can generally depend upon the nature of the electrolyte solution. For instance, while the discharge end 34 of the hollow capillary 22 and therefor the electrolyte solution 27 is typically is the powered (or input) electrode, and the counter electrode 34 is typically the output electrode, this is not a requirement of the device, and the opposite polarity can be established in other embodiments.

The LS-APGD affords the option of applying a voltage across the glow discharge space 35 in any of four ways: (1) the electrolytic solution grounded as the anode of the circuit; (2) the electrolytic solution powered as the anode of the circuit; (3) the electrolytic solution grounded as the cathode of the circuit; and (4) the electrolytic solution powered as the cathode of the circuit. The electrode that is at the more negative potential always serves as the cathode. For instance, in one embodiment, the electrically conducting element of the hollow capillary 22 can be electrically connected to the electrical power supply so as to become the powered (or input) electrode while the counter electrode 34 can become the output electrode.

As one of the discharge electrodes of the LS-APGD device 10 is the electrolytic solution 27, the passage of electrical current (either electrons or positive ions) across the solution/gas phase interface in the glow discharge space 35 can cause formation of the microplasma 36 and the volatilization/excitation/ionization of the solid sample 41 held the glow discharge space 35 upon contact with the microplasma 36. As with previously known LS-APGD devices, the LS-APGD device 10 can function so as to totally consume an aqueous electrolyte solution at a flow rate of up to about 2 mL/min, i.e., no water drips from the discharge end 24 of the capillary 22.

When the electrolyte solution 27 that has been electrified via the electrically conducting element 25 of the capillary 22 is consumed as it emerges from the discharge end 24 of the capillary 22, a microplasma 36 is created in the glow discharge space 35 between the emerging surface of the exiting electrified electrolyte solution 27 and the counter electrode 34. The microplasma can have i-V characteristics that are within the range of conventional (abnormal and normal) glow discharges operating in the 0.1 to 10 Torr pressure regime.

In accordance with one embodiment as illustrated in FIG. 2, a sheath/cooling/excitation gas can flow around at least a portion of the hollow capillary 122 including the discharge end 124. For example, the terminal portion of the hollow capillary 122 including the discharge end 124 can be surrounded by a conduit 131 such as a concentric cylinder. This conduit 131 can be connected to a gas supply such as helium, nitrogen or argon gas. The gas flow (indicated schematically by the arrows designated by the numeral 138) around the exterior of the discharge end 124 of the capillary 122 can keep the temperature of the discharge end 124 of the capillary 122 from exceeding the melting temperature of the materials that form the discharge end 124 of the capillary 122. Additionally, the gas 138 exiting from the annular space that is defined between the exterior of the discharge end 124 of the capillary 122 and the interior of the surrounding cylinder 131 is believed to confine the microplasma within the glow discharge space 135 more tightly around the longitudinal axis of the discharge end 124 of the capillary 122. Furthermore, the gas 138 exiting from the annular space that is defined between the exterior of the discharge end 124 of the capillary 122 and the interior of the surrounding cylinder 131 is believed to create an environment that is especially conducive to the formation of the microplasma and can help improve the temporal stability of the microplasma. In addition, it is believed that metastable atoms of the gas 138 can serve or assist in exciting the desorbed sample molecules of the sample 41. When included, the gas flow rate of a surrounding gas flow 138 can generally be from about 0.5 mL/min to about 2 L/min, for instance from about 1 mL/min to about 1 L/min in one embodiment.

During use, the LS-APGD device 10 can affect a series of processes that involve converting the solid sample 41 into a vapor-phase population, which then yields an analytically-relevant signal/signature. In the case of AD-OES, this means that analyte potentially leaving the solid substrate sample 41 in "molecular" form must be dissociated to isolated atoms that are eventually excited by plasma electrons and/or sheath gas (e.g., He) metastable atoms. While not wishing to be bound to any particular theory, it is believed that the volatilization mechanisms of the disclosed systems can include one or more of the three most commonly cited volatilization mechanisms including thermal energy, solvation followed by expulsion/vaporization, and fast excited state atoms.

However, there are a number of potential means of converting solid samples into the vapor phase analyte atoms with the LS-APGD device. Previous work with LS-APGD-produced microplasma has shown that temperatures as high as 300° C. can be realized on glass substrates. This level of thermal energy may well be sufficient to vaporize solution residue samples and thin 00 nm) metallic films, but is not high enough to vaporize bulk metals.

In some embodiments, the LS-APGD is sustained with an acid flow, e.g., 5% $HNO_3$, and acid dissolution may play a role in the volatilization. As the acidic feed solution is totally vaporized in the microplasma in this embodiment, a hot acidic vapor is likely impinging on the solid surface. This plasma effluent can produce an environment that can digest a variety of sample types, with the coincident heat yielding vaporized analyte. Additionally, it may be the case that volatile salts may be formed with the conjugate acid component, e.g., a nitrate conjugate acid component.

In conjunction with the desorption and ionization of the solid sample by use of the LS-APGD device 10, one or more instruments can be used to detect and analyze the excited state species that emits a characteristic response within the glow discharge space 35. By way of example, and as illustrated in FIG. 1, in one embodiment, a light directing element 50 can be disposed to direct the electromagnetic radiation from the glow discharge that forms in the glow discharge space 35 to a suitable analyzing instrument. A suitable light directing element can include a lens 50 and/or a fiber optic light guide. For example, one end of a 3 mm core diameter liquid light guide (available from Edmund Industrial Optics, Barington, N.J.) can be disposed so as to sample optical emission from the plasma 36 of the glow discharge formed in the glow discharge space 35. The opposite end of the light guide can be coupled to an instrument for analyzing electromagnetic radiation that emanates from the glow discharge. A suitable such analyzing instrument can include a monochromator or a polychromator.

By way of example, a light guide 50 can be coupled to the entrance slit 52 of an optical spectrometer 20 such as a Digikrom Model 240 monochromator (CVI Laser Corp., Albuquerque, N. Mex.) 0.24 m Czerny-Turner spectrometer equipped with a 2400 groove/mm holographic grating for optical analysis and monitoring of the emission from the sample. The control interface of the monochromator can be used to adjust the scanning range, slit width, spectral calibration, and wavelength selection of the monochromator, as is known.

The optical analysis instrument can be used in conjunction with other instruments, as is generally known in the art. For instance, a photo-multiplier tube (e.g., from Hamamatsu, Bridgewater, N.J. Model) can be disposed to detect the optical emission signals in the glow discharge. An analog current meter can be connected to the photo-multiplier tube and can convert the optical emission signals into voltage signals. A computer can be employed to record the output of the current meter e.g., via a National Instruments (Austin, Tex.) NB-MIO-16X interface board. An X-Y recorder-type program within the National Instruments LabView 2 software environment can be used to record the data. The obtained digital data can be processed and managed as desired.

The LS-APGD-based systems and methods disclosed herein possess the capabilities to volatilize surface species into the microplasma environment where analyte atoms can be excited and emit characteristic radiation that can be detected in a single step. The combination of the general operation space of the LS-APGD (low solution flow rates, low power, and small footprint) and the potential for using portable, array-based optical spectrometers matches well with methods that can be affected in the field.

The present disclosure may be better understood with reference to the Examples set forth below.

EXAMPLES

An LS-APGD device as shown in FIG. 1 was utilized. The plasma was composed of two electrodes including the liquid electrolyte fed via the capillary and the metal counter electrode. In a first case, a 75 μm i.d.×125 μm o.d. fused silica capillary tube was mounted coaxially within a 500 μm i.d.×700 μm o.d. stainless steel capillary tube. The electrolytic solution (5% (v/v) aqueous $HNO_3$) was utilized to sustain the discharge through its conductivity as well as to generate a predominately water-based plasma. A helium sheath gas flowed between the steel and glass capillaries at a rate of 0.6 L min$^{-1}$. The electrolyte solution was delivered by a syringe pump (NE-1000, New Era Pump System, Inc., Farmington, N.Y.) and the discharge was maintained by a Bertan Model 915 series power supply (Hickville, N.Y.) operated in the constant current mode, with a 10 kΩ ballast resistor placed in series with the powered electrode.

The counter electrode was a hollow stainless steel tube (500 μm i.d.×700 μm o.d.) through which helium gas flowed. The discharge current of the plasma operation was 60 mA with a potential of about 850 V, d.c. The microplasma counter electrode was mounted parallel to the sample substrate while the liquid electrode was pointed toward the sample substrate stage at an angle of about 60°.

In each of the runs, the spacing between the electrodes and the sample surface was set nominally at 2 mm, a distance that provides stable plasma operation but has not yet been rigorously evaluated. The sample surface was electrically-isolated (floating) relative to the discharge electrodes, and thus there were no directed charged particle interactions that might result in sputtering, etc.

Optical emission spectra and temporal emission transients were obtained on a CVI Laser (Albuquerque, N. Mex.) Digikrom 240 0.24 m monochromator system equipped with a Hamamatsu (Bridgewater, N.J.) R928 photomultiplier tube. Digital control of the scan functions and PMT signal monitoring was performed under the CVI Spectra AD III software environment. Optical emission from the microplasma was focused by a 75 mm focal length fused quartz lens onto the 50 μm-wide entrance slit of the monochromator. Spectral scans were performed at a rate of 100 nm$^{-1}$, with a signal integration time of 6 ms per 0.01 nm wavelength step. In the case of optical transient measurements, data were acquired at a rate of 10 points per second while sitting at a single wavelength position.

ACS-grade nitric acid used in the electrolytic solution flow was purchased from VWR (West Chester, Pa.). The nitric acid was diluted with de-ionized MilliQ water (DI-$H_2O$) (18.2 MΩ cm$^{-1}$, NANOpure Diamond Barnstead/Thermolyne Water System (Dubuque, Iowa)).

Solid materials were sampled in three forms; vapor-deposited thin films on mica substrates, dry residues of solutions deposited on mica substrates, and bulk metals. The metallic thin films were produced via evaporation of high purity metal under vacuum conditions and the deposition carried out normal to the mica substrate surface. Films of about 100 nm thickness were prepared. The solution residues were initially deposited as 1 μL of 500 μg mL$^{-1}$ aliquots of each nitrate salt applied onto the mica substrates (PELCO® Mica, Grade V5, 10×40 mm, Ted Pella, Inc. Redding, Calif.) multiple times successively as each layer dried under ambient conditions (about 3 min). The process was repeated four times for the Cu and Ag and eight times for Ni, with the residues covering an area of about 6 mm diameter. The substrates were further dried in a room-temperature desiccator for approximately eight hours prior to analysis. Finally, bulk Cu and Ni metals of stock grade and cut into 8 mm diameter disks were subjected to the LS-APGD.

The range of materials investigated posed different challenges in terms of thermal vaporization characteristics as well as susceptibility to acid dissolution, providing insights into possible sampling mechanisms. In addition, they demonstrated potential sample matrices for which AD-LS-APGD-OES can be employed.

Vapor-Deposited Thin Films

Figure 3:
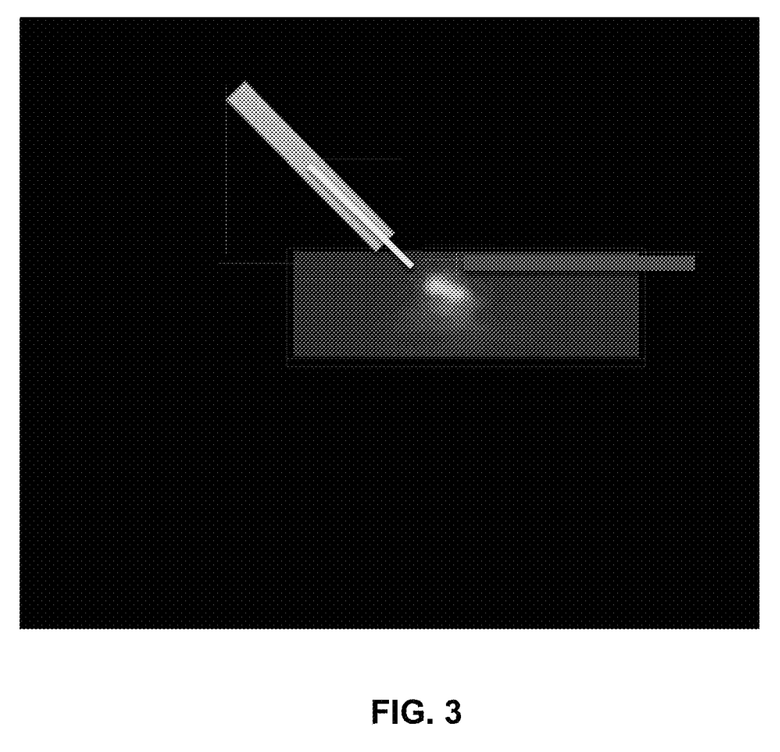
FIG. 3 is a photograph of a system during use.

FIG. 3 is a photograph of the system during examination of a copper thin film on a mica substrate. The photograph was taken through a 500-525 nm bandpass filter, revealing the atomic emission of Cu I transitions in that spectral region.

Metallic thin films constructed on simple mica substrates present a very homogeneous, sample form. Placement of the samples beneath the electrodes and ignition of the plasma resulted in the nearly immediate onset of vaporization as depicted in the optical transients of FIG. 4 at a) for Cu and at b) Ag thin films. The operating conditions for these samples included: discharge current=60 mA, sheath gas flow=0.6 L min$^{-1}$, counter electrode gas flow=0.5 L min$^{-1}$, and electrolyte solution flow rate=80 μL min$^{-1}$.

Figure 4:
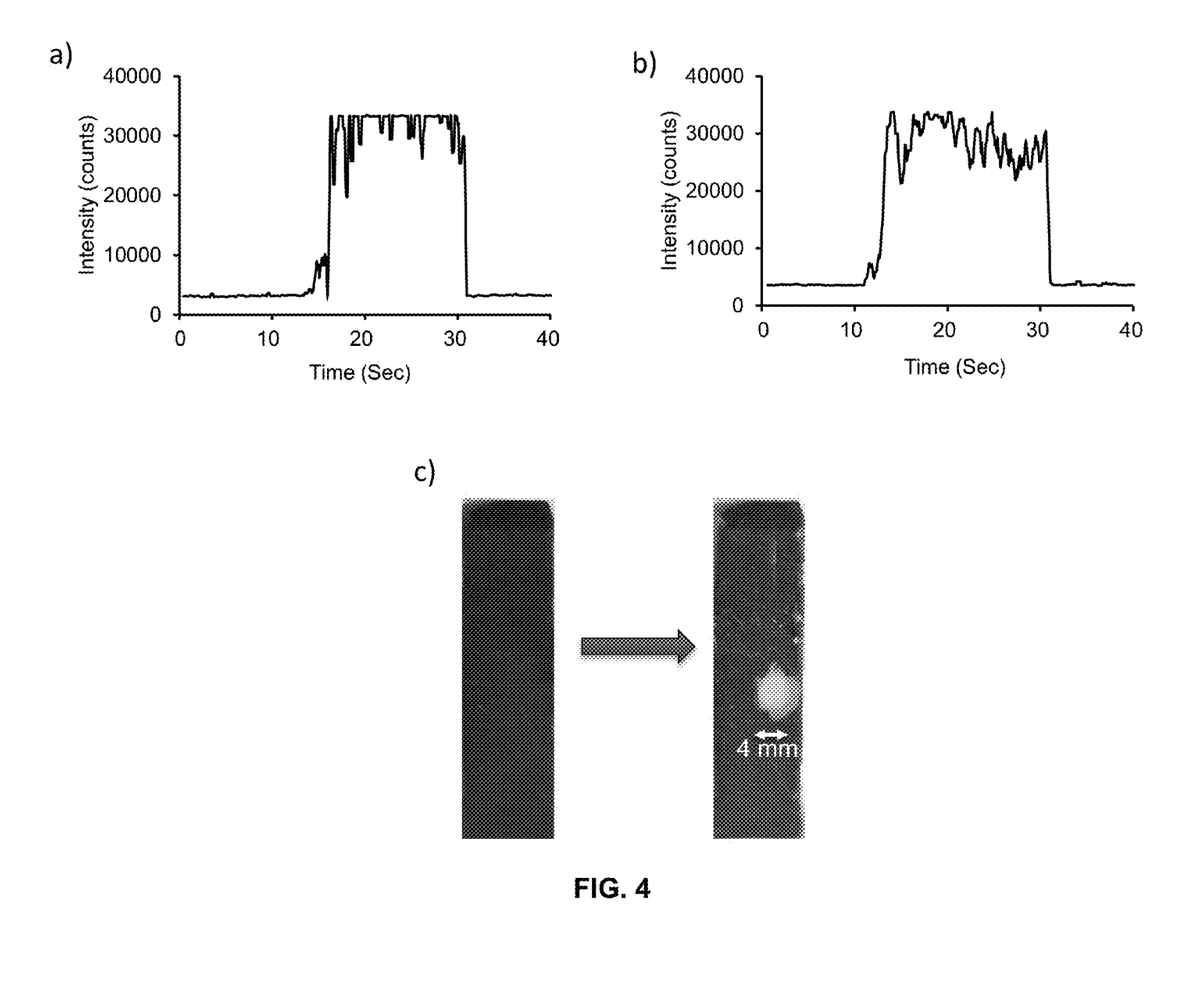
FIG. 4 presents at a) transient signals of copper vapor-deposited on to a mica substrate (Cu I at 324.7 nm) and presents at b) transient signals of silver vapor-deposited on to a mica substrate (Ag I at 328.1 nm). At c) is shown photographs of Cu-deposited mica substrate before (left) and after (right) exposure to the LS-APGD microplasma for a time period of about 15 s.

As seen in FIG. 4, there was a very rapid attainment of steady-state emission response for the monitored atomic transitions. The trailing edge reflects the total consumption of the metallic films in the region immediately beneath the microplasma. FIG. 4 at c) provides optical photographs of a Cu film prior to and after exposure to the microplasma. Given the general thickness of the films, and the sample removal area, it was estimated that a mass of ~25 μg of Cu was removed during the analysis. On a time basis, this reflects the signal representing about 1 μg s$^{-1}$, with high signal-to-background (S/B) characteristics. In terms of potential volatilization mechanisms, it is difficult to imagine that either thermal energy or fast atom bombardment are sufficient to excise the metal atoms from the solid film. On the other hand, both metals are readily dissolved in nitric acid under ambient conditions. Thus, it is not unreasonable that the high-temperature, acidic vapor can effectively vaporize these films.

Dry Solution Residues

Figure 5:
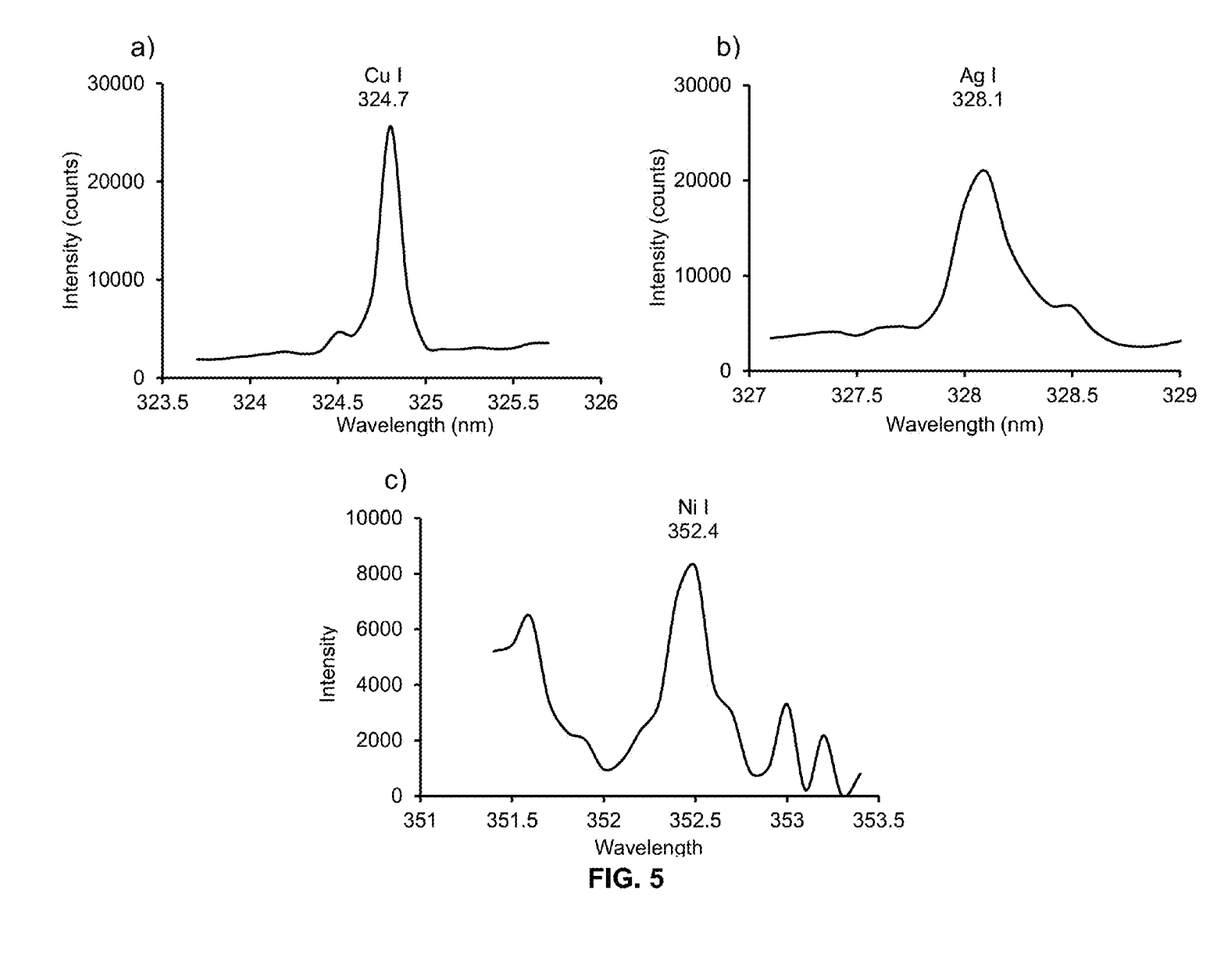
FIG. 5 presents AD-OES spectra of LS-APGD microplasma sampling of a) $Cu(NO_3)_2$, b) $AgNO_3$, and c) $Ni(NO_3)_2$ residues on mica substrates.

FIG. 5 provides optical emission spectral scans obtained for samples created by the deposition of Cu(NO$_3$)$_2$ (a), AgNO$_3$ (b), and Ni(NO$_3$)$_2$ (c) residues on mica substrates. Each element was deposited from 500 μg mL-1 solution, 4 μL for Cu and Ag, 84 for Ni. LS-APGD operating conditions: discharge current=60 mA, sheath gas flow=0.6 L min$^{-1}$, counter electrode gas flow=0.5 L min$^{-1}$, and electrolyte solution flow rate=80 μL min$^{-1}$.

It was difficult to visualize the location of the residues, and the distribution was far less uniform as compared to the metal films described above. In comparing the three elemental responses, the Cu I signal at a) shows much better intensities and S/B relative to Ag I at b) and Ni I at c). In the case of the Ni I, this transition occurred amongst a background N$_2$ band (which has been subtracted), reducing the spectral quality. The respective responses suggested that the sampling efficiencies were fairly uniform as Cu I and Ag I was expected to have a higher emission yields than Ni I.

If total consumption was achieved, the volatized masses would be 2 μg, 2 μg, and 4 μg for Cu, Ag, and Ni, respectively, based on application of the 4 and 8 μL sample volumes. It is difficult to imagine that total consumption is achieved, so these values suggest upper limits of the amount of material analyzed. Based on the measured signal-to-noise characteristics, the limits of detection (LODs) in mass units for these elements were 49, 99, and 400 ng, if total consumption of the residue was achieved.

Bulk Metal Samples

Figure 6:
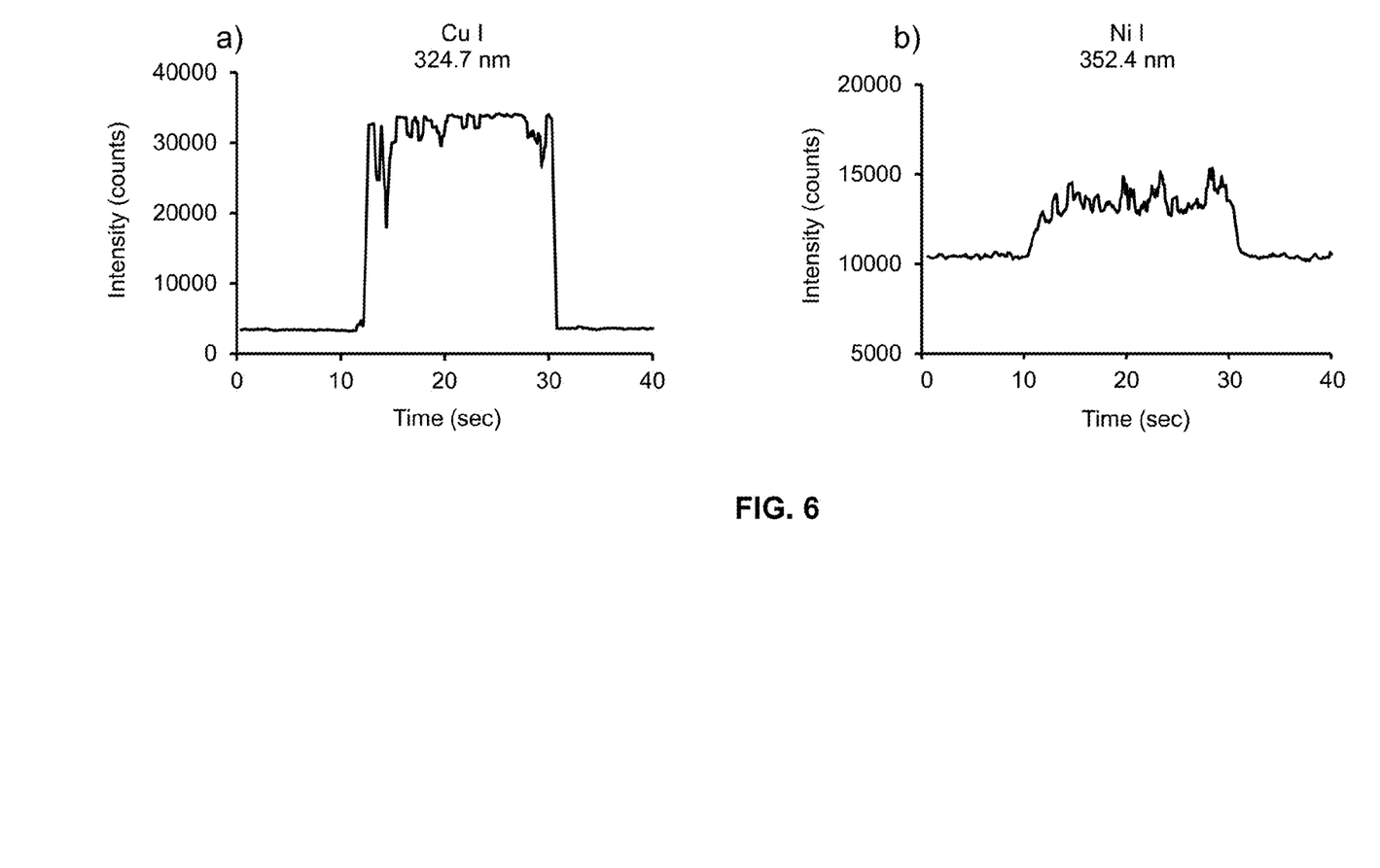
FIG. 6 provides transient emission responses of a) bulk copper (Cu I at 324.75 nm) and b) bulk nickel (Ni I at 352.4 nm).

FIG. 6 presents the AD-OES transients derived from bulk Cu (a) and Ni (a) metals. LS-APGD operating conditions: discharge current=60 mA, sheath gas flow=0.6 L min-1, counter electrode gas flow=0.5 L min-1, and electrolyte solution flow rate=80 μL min-1. Bulk metals represent the case where acid dissolution/vaporization is likely the predominate means of obtaining the gas phase analyte population. Neither 300° C. temperatures nor fast atom bombardment is likely sufficient to affect vaporization.

Different from the case of the metal films, the frontal and trailing edges of the transients are simply due to raising and lowering of the metal disks to the region of the microplasma source. As in the case of the metallic thin films, the responses were well-behaved in terms of temporal response and signal-to-background ratios. In the case of Ni I (c), the continuous N$_2$ band emission contributed to an appreciable background level. It is imagined that the OES responses could continue over more extended periods of time, perhaps resulting in a depth-profiling capability.

Cu is quite soluble in aqueous HNO$_3$, while metallic Ni is most easily dissolved in mixtures of HCl and H$_2$O$_2$. Solutions of boiling, >65% HNO$_3$ are typically needed to dissolve bulk Ni. If acid dissolution was the operable mechanism for solid sampling in the LS-APGD, one would expect that Cu would indeed generate a large analytical response and Ni not so much; the potential for very large matrix effects. In fact, to have both species' OES transitions yield values of the same order of magnitude seems to suggest that indeed, Ni is quite well vaporized. Herein, we see that it is perhaps the ability to generate high densities of H$_3$O$^+$ in the vapor phase at elevated temperatures that is the important reactive species, and not the identity of the starting acid (or more specifically the conjugate base) that allows vaporization of these diverse materials. Another potential mechanism could be the formation of volatile nickel nitrate salt. Changing the acid identity or operating the microplasma with a salt electrolyte such as NaCl instead of an acid at all could provide further insights to the processes.

While certain embodiments of the disclosed subject matter have been described using specific terms, such description is for illustrative purposes only, and it is to be understood that changes and variations may be made without departing from the spirit or scope of the subject matter.

What is claimed is:

1. A method for examining a sample comprising:
   flowing an electrolyte solution through a first hollow tube from a first end to a second end of the first hollow tube;
   flowing a gas through a second hollow tube from a first end to a second end of the second hollow tube, the second hollow tube comprising counter electrode;
   forming a microplasma in a glow discharge space of a liquid sampling atmospheric pressure glow discharge (LS-APGD) device, the glow discharge space being defined between the second end of the first hollow tube and the second end of the second hollow tube;
   contacting a solid sample within the glow discharge space with the microplasma and with the gas and thereby volatilizing the solid sample to release one or more components of the solid sample and exciting the released components, the excited components emitting a characteristic response within the glow discharge space; and
   optically detecting the characteristic response as the emission occurs within the glow discharge space.

2. The method of claim 1, wherein the solid sample comprises a metallic film.

3. The method of claim 1, wherein the solid sample comprises a dried solution residue.

4. The method of claim 1, wherein the solid sample comprises a metal.

5. The method of claim 1, wherein the solid sample comprises a soil.

6. The method of claim 1, wherein the method is carried out in the field.

7. The method of claim 1, wherein the method is free of sample preparation.

8. The method of claim 1, wherein the microplasma comprises a reference material, the reference material emitting a second characteristic response within the glow discharge space, the method further comprising optically detecting the second characteristic response.

9. The method of claim 1, wherein the solid sample is electrically isolated from the LS-APGD device.

10. The method of claim 1, wherein the solid sample is within an electrical circuit of the LS-APGD device.

11. The method of claim 1, further comprising modifying the size and/or configuration of the glow discharge space by selective motion of the end of the first hollow tube or the counter electrode.

12. The method of claim 1, wherein the gas that flows through the second hollow tube is an inert gas.

13. The method of claim 1, the step of forming the microplasma comprising developing a voltage difference between the electrolyte solution expelled from the second end of the first hollow tube and the counter electrode.

14. The method of claim 1, further comprising flowing a gas along at least a portion of the exterior surface of the first hollow tube.

15. The method of claim 1, wherein the gas flowing through the second hollow tube comprises helium, nitrogen, or argon.

16. The method of claim 1, the step of forming the microplasma comprising developing a voltage difference across the glow discharge space by use of a power supply selected from a direct current source, a radio frequency power source, or a microwave frequency power source.

17. The method of claim 1, the step of optically detecting the characteristic response comprising directing light from the glow discharge space to an optical spectrometer.

18. The method of claim 1, wherein the axis of the first hollow tube is at an angle of less than 90° to the axis of the second hollow tube.

19. The method of claim 1, wherein the axis of the first hollow tube is at an angle of from 90° to 180° to the axis of the second hollow tube.

20. The method of claim 1, wherein the axis of the first hollow tube is at an angle of from 90° to 120° to the axis of the second hollow tube.

* * * * *